(12) United States Patent
Boyd et al.

(10) Patent No.: US 7,914,537 B2
(45) Date of Patent: Mar. 29, 2011

(54) DEVICES AND METHODS FOR THE RESTORATION OF A SPINAL DISC

(75) Inventors: Lawrence M. Boyd, Durham, NC (US); Maureen L. Upton, Durham, NC (US)

(73) Assignee: Spine Wave, Inc., Shelton, CT (US)

( * ) Notice: Subject to any disclaimer, the term of this patent is extended or adjusted under 35 U.S.C. 154(b) by 232 days.

(21) Appl. No.: 12/275,774

(22) Filed: Nov. 21, 2008

(65) Prior Publication Data
US 2009/0131946 A1    May 21, 2009

Related U.S. Application Data

(63) Continuation of application No. 10/667,540, filed on Sep. 22, 2003, now Pat. No. 7,575,577, which is a continuation of application No. 10/282,755, filed on Oct. 29, 2002, now Pat. No. 7,004,945.

(60) Provisional application No. 60/336,333, filed on Nov. 1, 2001, provisional application No. 60/336,002, filed on Nov. 1, 2001.

(51) Int. Cl.
*A61B 17/58* (2006.01)

(52) U.S. Cl. ............................... 606/92; 606/93; 606/94

(58) Field of Classification Search ............. 606/90–94, 606/99, 246, 247, 279, 86 R; 424/93.1, 94.63; 604/19, 500, 506, 164.11; 514/12; 128/898
See application file for complete search history.

(56) References Cited

U.S. PATENT DOCUMENTS

| | | | | |
|---|---|---|---|---|
| 5,888,220 | A * | 3/1999 | Felt et al. ................... | 128/898 |
| 6,017,350 | A | 1/2000 | Long | |
| 6,018,094 | A * | 1/2000 | Fox .............................. | 606/191 |
| 6,506,214 | B1 * | 1/2003 | Gross ......................... | 623/19.11 |
| 6,620,162 | B2 | 9/2003 | Kuslich et al. | |
| 6,716,216 | B1 * | 4/2004 | Boucher et al. ............ | 606/86 R |
| 6,852,095 | B1 | 2/2005 | Ray | |
| 7,004,945 | B2 * | 2/2006 | Boyd et al. ................. | 606/92 |
| 7,575,577 | B2 * | 8/2009 | Boyd et al. ................. | 606/92 |

* cited by examiner

*Primary Examiner* — Pedro Philogene
(74) *Attorney, Agent, or Firm* — Hoffmann & Baron, LLP

(57) ABSTRACT

A system and method is provided for maintaining a proper intervertebral disc height during the replacement or augmentation of the spinal disc. In one embodiment, a cannulated distractor is used to distract the adjacent vertebrae and maintain a proper disc space height. The cannulated distractor is fluidly connected to a source of fluent material for injection into the disc space. The distraction includes a distraction tip resident within the disc space that includes a central lumen and a number of openings communicating with the lumen to dispense the fluent material within the disc space.

21 Claims, 6 Drawing Sheets

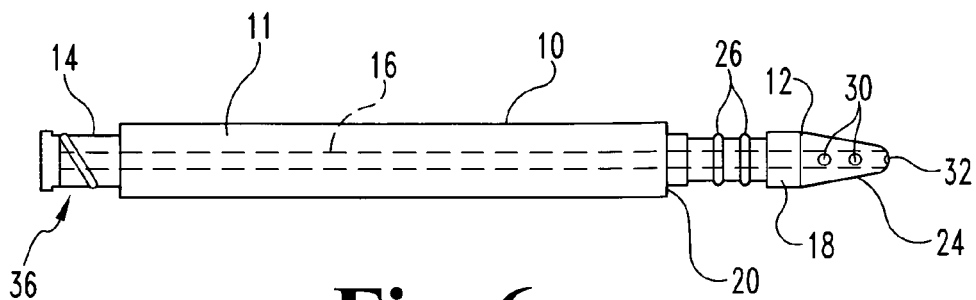
Fig. 6
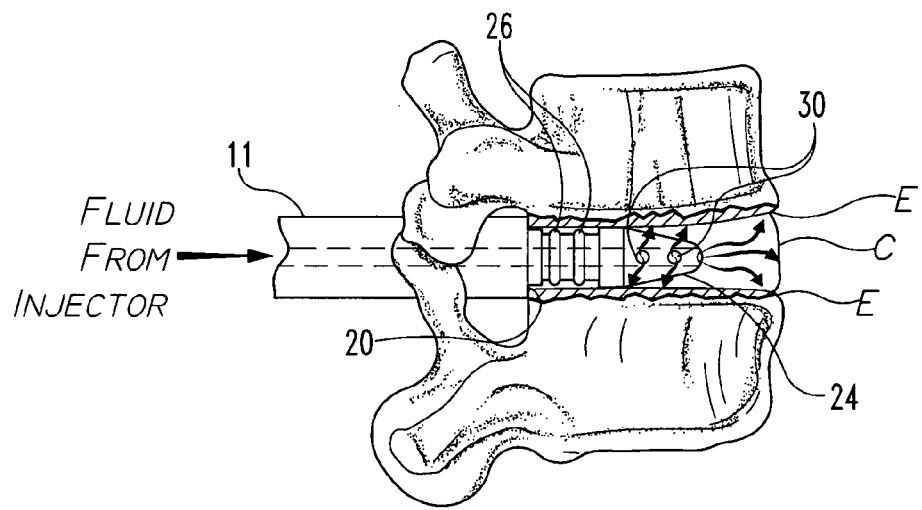
Fig. 7
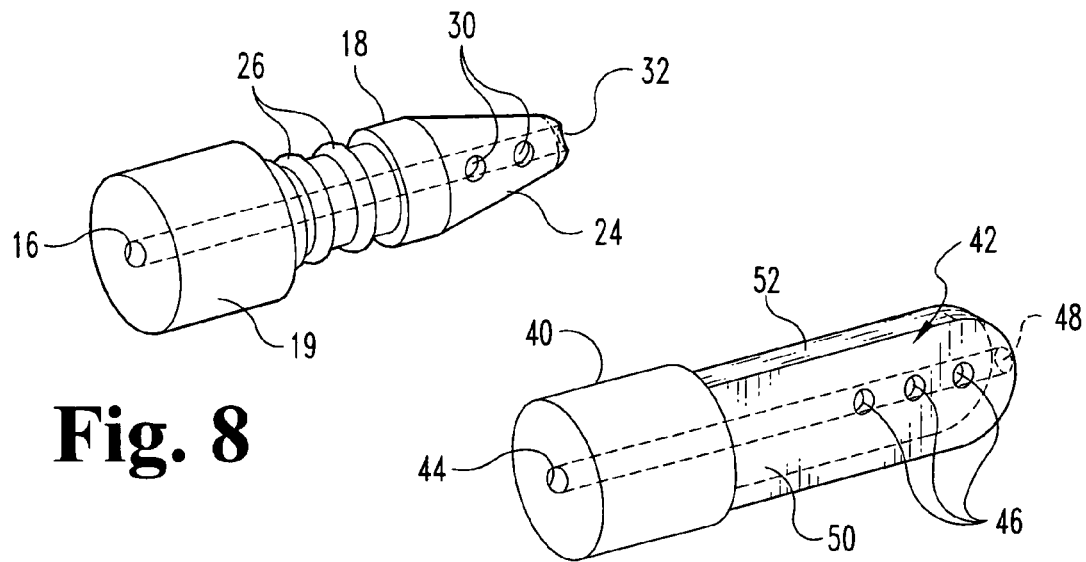
Fig. 8
Fig. 9

DEVICES AND METHODS FOR THE RESTORATION OF A SPINAL DISC

REFERENCE TO RELATED APPLICATIONS

This application is a continuation of application Ser. No. 10/667,540, filed on Sep. 22, 2003, which is a continuation of application Ser. No. 10/282,755, filed on Oct. 29, 2002 in the name of the same inventor, which issued on Feb. 28, 2006, as U.S. Patent No. 7,004,945, and which claims priority to provisional application Ser. No. 60/336,002, entitled "Devices, Methods and Assemblies for Intervertebral Disc Repair and Regeneration", and provisional application Ser. No. 60/336,333, entitled "Pretreatment of Cartilaginous Endplates Prior to Treatment of the Intervertebral Disc with an Injectable Biomaterial", both of which were filed on Nov. 1, 2001, and the disclosure of which are both incorporated herein by reference.

BACKGROUND OF THE INVENTION

The present invention relates generally to the treatment of spinal diseases and injuries, and more specifically to the restoration of the spinal disc following surgical treatment. The invention contemplates devices and methods for restoring the normal intervertebral disc space height and for facilitating the introduction of biomaterials for use in the repair and restoration of the intervertebral disc.

The intervertebral disc is divided into two distinct regions: the nucleus pulposus and the annulus fibrosus. The nucleus lies at the center of the disc and is surrounded and contained by the annulus. The annulus contains collagen fibers that form concentric lamellae that surround the nucleus and insert into the endplates of the adjacent vertebral bodies to form a reinforced structure. Cartilaginous endplates are located at the interface between the disc and the adjacent vertebral bodies.

The intervertebral disc is the largest avascular structure in the body. The disc receives nutrients and expels waste by diffusion through the adjacent vascularized endplates. The hygroscopic nature of the proteoglycan matrix of the nucleus operates to generate high intra-nuclear pressure. As the water content in the disc increases, the intra-nuclear pressure increases and the nucleus swells to increase the height of the disc. This swelling places the fibers of the annulus in tension. A normal disc has a height of about 10-15 mm.

There are many causes of disruption or degeneration of the intervertebral disc that can be generally categorized as mechanical, genetic and biochemical. Mechanical damage includes herniation in which a portion of the nucleus pulposus projects through a fissure or tear in the annulus fibrosus. Genetic and biochemical causes can result in changes in the extracellular matrix pattern of the disc and a decrease in biosynthesis of extracellular matrix components by the cells of the disc. Degeneration is a progressive process that usually begins with a decrease in the ability of the extracellular matrix in the central nucleus pulposus to bind water due to reduced proteoglycan content. With a loss of water content, the nucleus becomes desiccated resulting in a decrease in internal disc hydraulic pressure, and ultimately to a loss of disc height. This loss of disc height can cause the annulus to buckle with non-tensile loading and the annular lamellae to delaminate, resulting in annular fissures. Herniation may then occur as rupture leads to protrusion of the nucleus.

Proper disc height is necessary to ensure proper functionality of the intervertebral disc and spinal column. The disc serves several functions, although its primary function is to facilitate mobility of the spine. In addition, the disc provides for load bearing, load transfer and shock absorption between vertebral levels. The weight of the person generates a compressive load on the discs, but this load is not uniform during typical bending movements. During forward flexion, the posterior annular fibers are stretched while the anterior fibers are compressed. In addition, a translocation of the nucleus occurs as the center of gravity of the nucleus shifts away from the center and towards the extended side.

Changes in disc height can have both local and global effects. On the local (or cellular, level) decreased disc height results in increased pressure in the nucleus, which can lead to a decrease in cell matrix synthesis and an increase in cell necrosis and apoptosis. In addition, increases in intra-discal pressure create an unfavorable environment for fluid transfer into the disc, which can cause a further decrease in disc height.

Decreased disc height also results in significant changes in the global mechanical stability of the spine. With decreasing height of the disc, the facet joints bear increasing loads and may undergo hypertrophy and degeneration, and may even act as a source of pain over time. Decreased stiffness of the spinal column and increased range of motion resulting from loss of disc height can lead to further instability of the spine, as well as back pain. The outer annulus fibrosus is designed to provide stability under tensile loading, and a well-hydrated nucleus maintains sufficient disc height to keep the annulus fibers properly tensioned. With decreases in disc height, the annular fibers are no longer able to provide the same degree of stability, resulting in abnormal joint motion. This excessive motion can manifest itself in abnormal muscle, ligament and tendon loading, which can ultimately be a source of back pain.

Radicular pain may result from a decrease in foraminal volume caused by decreased disc height. Specifically, as disc height decreases, the volume of the foraminal canal, through which the spinal nerve roots pass, decreases. This decrease may lead to spinal nerve impingement, with associated radiating pain and dysfunction Finally, adjacent segment loading increases as the disc height decreases at a given level. The discs that must bear additional loading are now susceptible to accelerated degeneration and compromise, which may eventually propagate along the destabilized spinal column.

In spite of all of these detriments that accompany decreases in disc height, where the change in disc height is gradual many of the ill effects may be "tolerable" to the spine and may allow time for the spinal system to adapt to the gradual changes. However, the sudden decrease in disc volume caused by the surgical removal of the disc or disc nucleus may heighten the local and global problems noted above. Many disc defects are treated through a surgical procedure, such as a discectomy in which the nucleus pulposus material is removed. During a total discectomy, a substantial amount (and usually all) of the volume of the nucleus pulposus is removed and immediate loss of disc height and volume can result. Even with a partial discectomy, loss of disc height can ensue. Discectomy alone is the most common spinal surgical treatment, frequently used to treat radicular pain resulting from nerve impingement by disc bulge or disc fragments contacting the spinal neural structures.

In another common spinal procedure, the discectomy may be followed by an implant procedure in which a prosthesis is introduced into the cavity left in the disc space when the nucleus material is removed. Thus far, the most prominent prosthesis is a mechanical device or a "cage" that is sized to restore the proper disc height and is configured for fixation between adjacent vertebrae. These mechanical solutions take on a variety of forms, including solid kidney-shaped implants, hollow blocks filled with bone growth material, push-in implants and threaded cylindrical cages.

In more recent years, injectable biomaterials have been more widely considered as an augment to a discectomy. As early as 1962, Alf Nachemson suggested the injection of room temperature vulcanizing silicone into a degenerated disc using an ordinary syringe. In 1974, Lemaire and others reported on the clinical experience of Schulman with an in situ polymerizable disc prosthesis. Since then, many injectable biomaterials or scaffolds have been developed as a substitute for the disc nucleus pulposus, such as hyaluronic acid, fibrin glue, alginate, elastin-like polypeptides, collagen type I gel and others. A number of patents have issued concerning various injectable biomaterials including: cross-linkable silk elastin copolymer discussed in U.S. Pat. No. 6,423,333 (Stedronsky et al.); U.S. Pat. No. 6,380,154 (Capello et al.); U.S. Pat. No. 6,355,776 (Ferrari et al.); U.S. Pat. No. 6,258,872 (Stedronsky et al.); U.S. Pat. No. 6,184,348 (Ferrari et al.); U.S. Pat. No. 6,140,072 (Ferrari et al.); U.S. Pat. No. 6,033,654 (Stedronsky et al.); U.S. Pat. No. 6,018,030 (Ferrari et al.); U.S. Pat. No. 6,015,474 (Stedronsky); U.S. Pat. No. 5,830,713 (Ferrari et al.); U.S. Pat. No. 5,817,303 (Stedronsky et al.); U.S. Pat. No. 5,808,012 (Donofrio et al.); U.S. Pat. No. 5,773,577 (Capello); U.S. Pat. No. 5,773,249 (Capello et al.); U.S. Pat. No. 5,770,697 (Ferrari et al.); U.S. Pat. No. 5,760,004 (Stedronsky); U.S. Pat. No. 5,723,588 (Donofrio); U.S. Pat. No. 5,641,648 (Ferrari); and U.S. Pat. No. 5,235,041 (Capello et al.); protein hydrogel described in U.S. Pat. No. 5,318,524 (Morse et al.); U.S. Pat. No. 5,259,971 (Morse et al.): U.S. Pat. No. 5,219,328 (Morse et al.); and U.S. Pat. No. 5,030,215; polyurethane-filled balloons discussed in 60/004,710 (Felt et al.); U.S. Pat. No. 6,306,177 (Felt et al.); U.S. Pat. No. 6,248,131 (Felt et al.) and U.S. Pat. No. 6,224,630 (Bao et al.); collagen-PEG set forth in U.S. Pat. No. 6,428,978 (Olsen et al.); U.S. Pat. No. 6,413,742 (Olsen et al.); U.S. Pat. No. 6,323,278 (Rhee et al.); U.S. Pat. No. 6,312,725 (Wallace et al.); U.S. Pat. No. 6,277,394 (Sierra); U.S. Pat. No. 6,166,130 (Rhee et al.); U.S. Pat. No. 6,165,489 (Berg et al.); U.S. Pat. No. 6,123,687 (Simonyi et al.); U.S. Pat. No. 6,111,165 (Berg); U.S. Pat. No. 6,110,484 (Sierra); U.S. Pat. No. 6,096,309 (Prior et al.); U.S. Pat. No. 6,051,648 (Rhee et al.); U.S. Pat. No. 5,997,811 (Esposito et al.); U.S. Pat. No. 5,962,648 (Berg); U.S. Pat. No. 5,936,035 (Rhee et al.); and U.S. Pat. No. 5,874,500 (Rhee et al.); chitosan in U.S. Pat. No. 6,344,488 to Chenite et al.; a variety of polymers discussed in U.S. Pat. No. 6,187,048 (Milner et al.; recombinant biomaterials in 60/038,150 (Urry); U.S. Pat. No. 6,004,782 (Daniell et al.); U.S. Pat. No. 5,064,430 (Urry); U.S. Pat. No. 4,898,962 (Urry); U.S. Pat. No. 4,870,055 (Urry); U.S. Pat. No. 4,783,523 (Urry et al.); U.S. Pat. No. 4,783,523 (Urry et al.); U.S. Pat. No. 4,589,882 (Urry); U.S. Pat. No. 4,500,700 (Urry); U.S. Pat. No. 4,474,851 (Urry); U.S. Pat. No. 4,187,852 (Urry et al.); and U.S. Pat. No. 4,132,746 (Urry et al.); and annulus repair materials described in U.S. Pat. No. 6,428,576 to Haldimann.

These references disclose biomaterials or injectable scaffolds that have one or more properties that are important to disc replacement, including strong mechanical strength, promotion of tissue formation, biodegradability, biocompatibility, sterilizability, minimal curing or setting time, optimum curing temperature, and low viscosity for easy introduction into the disc space. The scaffold must exhibit the necessary mechanical properties as well as provide physical support. It is also important that the scaffold be able to withstand the large number of loading cycles experienced by the spine. The biocompatibility of the material is of utmost importance. Neither the initial material nor any of its degradation products should elicit an unresolved immune or toxicological response, demonstrate immunogenicity, or express cytoxicity.

Generally, the above-mentioned biomaterials are injected as viscous fluids and then cured in situ. Curing methods include thermosensitive cross-linking, photopolymerization, or the addition of a solidifying or cross-linking agent. The setting time of the material is important—it should be long enough to allow for accurate placement of the biomaterial during the procedure yet should be short enough so as not to prolong the length of the surgical procedure. If the material experiences a temperature change while hardening, the increase in temperature should be small and the heat generated should not damage the surrounding tissue. The viscosity or fluidity of the material should balance the need for the substance to remain at the site of its introduction into the disc, with the ability of the surgeon to manipulate its placement, and with the need to assure complete filling of the intradiscal space or voids.

Regardless of the injectable scaffold material used, it is critical that the completed procedure restore the disc height. It is thus important that the proper disc height be maintained while the biomaterial is being introduced into the intradiscal space. Ideally, the disc height will be restored to levels equivalent to the heights of the adjacent discs and representative of a normal spinal disc height for the particular patient.

However, if disc height is not re-established prior to introduction of the scaffold material, it will become impossible to replace the lost disc volume and at least restore the disc height to what it was prior to the discectomy. Failure to hold a proper disc height as the biomaterial is introduced and cured in situ can eventually lead to a collapse of the disc space. This phenomenon is illustrated by a comparison of a proper intervertebral disc height in FIG. 1a versus a reduced disc height in FIG. 1b. The reduced disc height of FIG. 1b will ordinarily follow a substantially complete discectomy, unless the adjacent vertebrae are distracted. The patient can be placed in certain positions that tend to open the disc space, particularly at the posterior side of the disc D. However, it has been found that even with hyper-flexion of the spine the intervertebral space does not approach its proper volume, and consequently the intervertebral height does not approach the proper disc height of FIG. 1a.

Prior procedures for the implantation of a curable disc prosthesis have relied upon the physical positioning of the patient or upon pressurized injection of the biomaterial to obtain some degree of distraction. However, these prior approaches do not achieve repeatable restoration of proper anatomical disc height, either during the surgical procedure or afterwards. Consequently, there remains a need for a method and system that provides a high degree of assurance that a proper disc height will be established and maintained when the intervertebral disc is replaced or augmented by an injectable biomaterial.

SUMMARY OF THE INVENTION

In order to address the unresolved needs of prior spinal procedures, the present invention contemplates a method for injecting a fluent material into a disc space. The method includes the steps of creating a portal in the annulus pulposus in communication with the intradiscal space and impacting a cannulated distractor into the portal. In accordance with one feature of the invention, the distractor is configured to distract the vertebrae adjacent the intradiscal space and to establish a disc space height between the adjacent vertebrae. The method includes the further step of introducing the fluent material into the intradiscal space through a lumen of the cannulated distractor while the distractor maintains the established disc space height.

In certain embodiments, the inventive method includes the step of performing a discectomy after the portal is created, in which the discectomy forms a cavity within the intradiscal space. In this embodiment, the step of impacting a cannulated distractor includes positioning the distractor so that the lumen is in communication with the cavity, and the step of introducing the fluid includes introducing the fluid into the cavity. The discectomy can be a total discectomy in which substantially all of the nucleus pulposus is removed from the disc space.

In a further feature of the invention, the fluent material is a curable biomaterial that is particularly suited as a disc replacement or augmentation material. In this case, the step of introducing the fluent material can include maintaining the distractor in its impacted position until the biomaterial cures in situ. In other words, the cannulated distractor maintains the adjacent vertebrae in their distracted position until the biomaterial has set. In this way, the proper disc height can be maintained and retained once the biomaterial has set and the distractor removed.

In certain embodiments, the fluent material can be introduced into the disc cavity under pressure. In another feature of the invention that is particularly useful where the fluent material is under pressure, the cannulated distractor is configured to seal the portal when the distractor is impacted therein. In some embodiments, the distractor has a portion sized to substantially block or seal the annular portal. In other embodiments, the distractor includes a sealing feature that bears against the adjacent vertebrae and/or the annulus fibrosus material surrounding the portal. The sealing feature can be integral with the cannulated distractor or can include a separate component, such as a seal ring, mounted on the distractor.

In still another aspect of the invention, and again one that is particularly suited where the fluent material is under pressure, a vent is provided in the cannulated distractor. Thus, the fluent material can be introduced into the intradiscal space until the fluent material seeps from the vent. Thus, the vent can provide an immediate indication that the disc cavity is full.

In some embodiments of the invention, the cannulated distractor is engaged to a fluid injector apparatus. This apparatus can be in a variety of forms, including a pump, a syringe and a gravity feed system.

In other embodiments, the step of introducing the fluent material includes extending an tube through the lumen in the cannulated distractor, with the tube fluidly connected to a source of the fluent material. The tube can be manipulated through the distractor lumen to direct the fluent material to specific locations within the disc cavity. For instance, the tube can be moved through a seeping motion so that the fluent material is completely dispersed throughout the disc space. At the same time, the tube can be gradually withdrawn from the distractor lumen as the fluent material nears the lumen opening.

In a preferred embodiment, a seal is provided between the tube and the lumen. A vent can then be provided separate from the lumen so that the fluent material can seep from the vent to indicate that the cavity is full.

In another embodiment of the invention, a device for injecting a fluent material into a disc space comprises a distraction member having opposite surfaces configured to distract adjacent vertebrae to the disc space. The distraction member has a proximal end and a distal end portion, in which at least the distal end portion configured to be disposed within the disc space. The distraction member further defines a fluid passageway between the proximal end and the distal end portion, the passageway having an opening at the proximal end and at the distal end portion. In some embodiments, the distraction member can include a fitting associated with the proximal end of the distraction member for fluidly connecting the distraction member to a source of the fluent material.

In accordance with another aspect of the invention, the device further comprises an elongated cannula defining a lumen therethrough. The cannula can have a first fitting at one end thereof configured for fluid tight connection to the fitting of the distraction member, and a second fitting at an opposite end thereof configured for fluid connection to a source of the fluent material. In specific embodiments, the distraction member is integral with the cannula and the second fitting is the fitting associated with the proximal end of the distraction member. In other embodiments, the distraction member is removable from the cannula.

In a preferred embodiment, at least the distal end portion of the distraction member is bullet-shaped. In alternative embodiments, the distal end portion of is wedge-shaped with opposite substantially flat sides, cruciate-shaped, I-beam shaped and C-shaped.

The fluid passageway of the distraction member includes a central lumen with a number of openings communicating therewith. The openings can be arranged in the variously shaped distal end portion to direct the fluent material to appropriate locations within the disc cavity. The distraction member can also define a vent opening separate from the fluid passageway. In certain embodiments, the fluid passageway can be in the form of interconnected interstices throughout the distraction member material.

In the preferred embodiment, the distraction member is formed of a biocompatible material, such as stainless steel or titanium. In alternative embodiments, other biocompatible materials can be used, such as polymeric materials and even bioresorbable materials. In accordance with one aspect, the distraction member is configured to be removed from the disc space once the fluent material has been introduced into the disc cavity, and has cured, if necessary. In other aspects, the distraction member is configured to remain within the disc space, most preferably if the member is formed of a bioresorbable material.

The distraction member can include a sealing element associated with a proximal portion of the distal end portion, wherein the sealing element is configured to provide a substantially fluid-tight seal within the disc space. The sealing element can include a number of seal rings disposed on the distal end portion. The seal rings can be integral with the distal end portion or can be elastomeric rings mounted on the distal end portion, for example.

It is one object of the invention to provide a system and device for maintaining and enforcing a proper intervertebral spacing or disc height when a disc prosthesis is introduced into a cavity within the intradiscal space. Another object is achieved by features of the invention that allow introduction of a fluent material into the disc space while maintaining the adjacent vertebrae distracted and the disc height intact.

Other objects and certain benefits of the invention can be discerned from the following written description and accompanying figures.

DESCRIPTION OF THE FIGURES

FIG. 6 is a side view of a cannulated distractor in accordance with one embodiment of the present invention.

FIG. 7 is a lateral view of the disc space shown in FIGS. 2-5 with the cannulated distractor of FIG. 6 positioned within the disc space.

FIG. 8 is a perspective view of a distraction tip forming part of the cannulated distractor shown in FIGS. 6 and 7.

FIG. 9 is a perspective view of a distraction tip according an alternative embodiment of the invention.

DESCRIPTION OF THE PREFERRED EMBODIMENTS

Figure 1A:
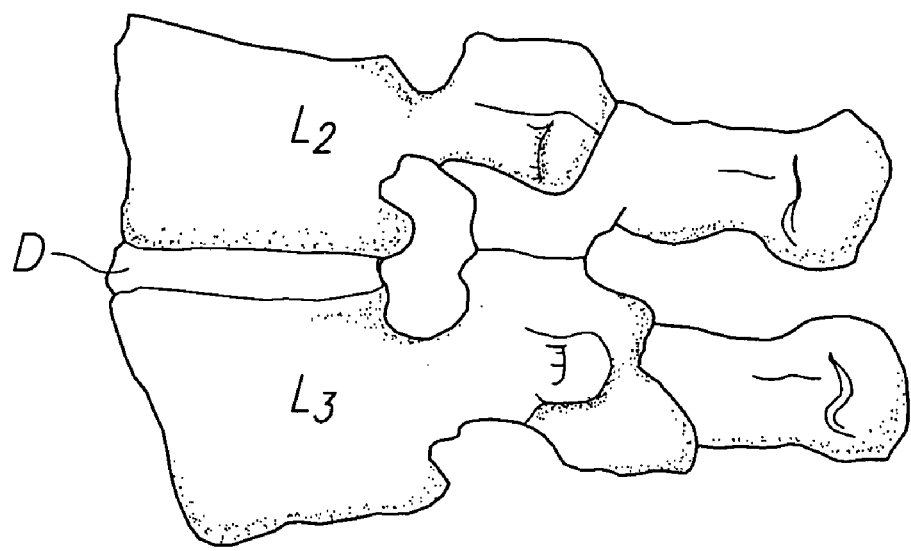
FIGS. 1a-1b are lateral views of a disc and adjacent vertebrae showing a proper intervertebral disc height (FIG. 1a) and a reduced disc height (FIG. 1b) following a substantially complete discectomy.
Figure 1B:
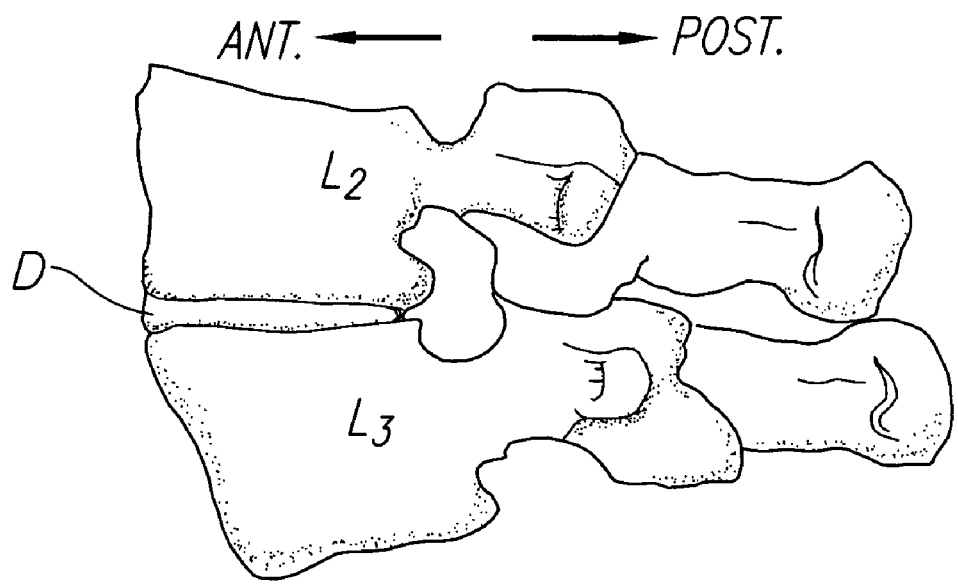

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates a procedure and device that is implemented following removal of a portion or substantially all of the natural nucleus pulposus of an intervertebral disc. One important purpose of the invention is to maintain the proper disc height during the introduction of a biomaterial that is intended to replace the removed nuclear material. Removal of disc material can be accomplished chemically, such as by the use of Chymopapain. However, the more common approach is by discectomy, which can be conducted as an open surgical procedure, via microscope-assisted visualization, or through percutaneous access.

Figure 2:
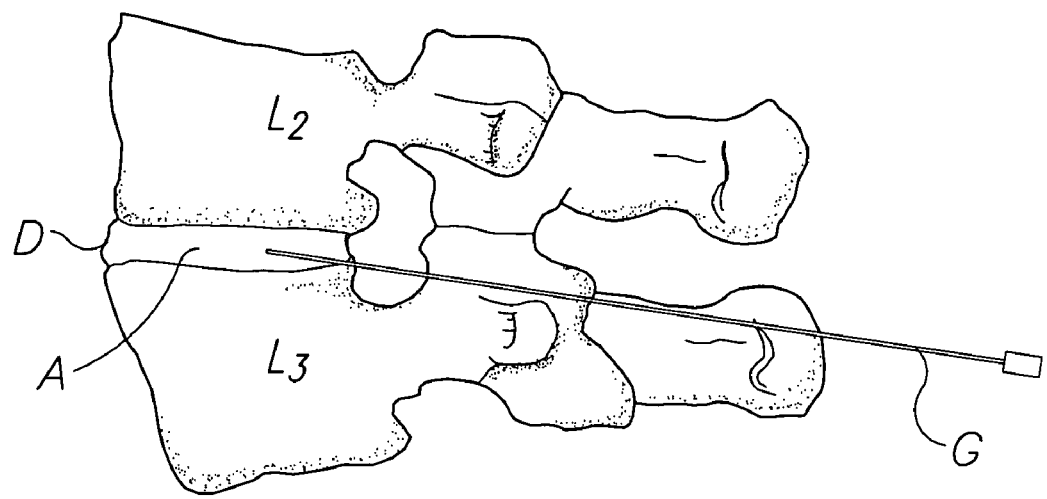
FIG. 2 is a lateral view a disc and adjacent vertebrae with a guide wire placed in accordance with one aspect of the present invention.
Figure 3:
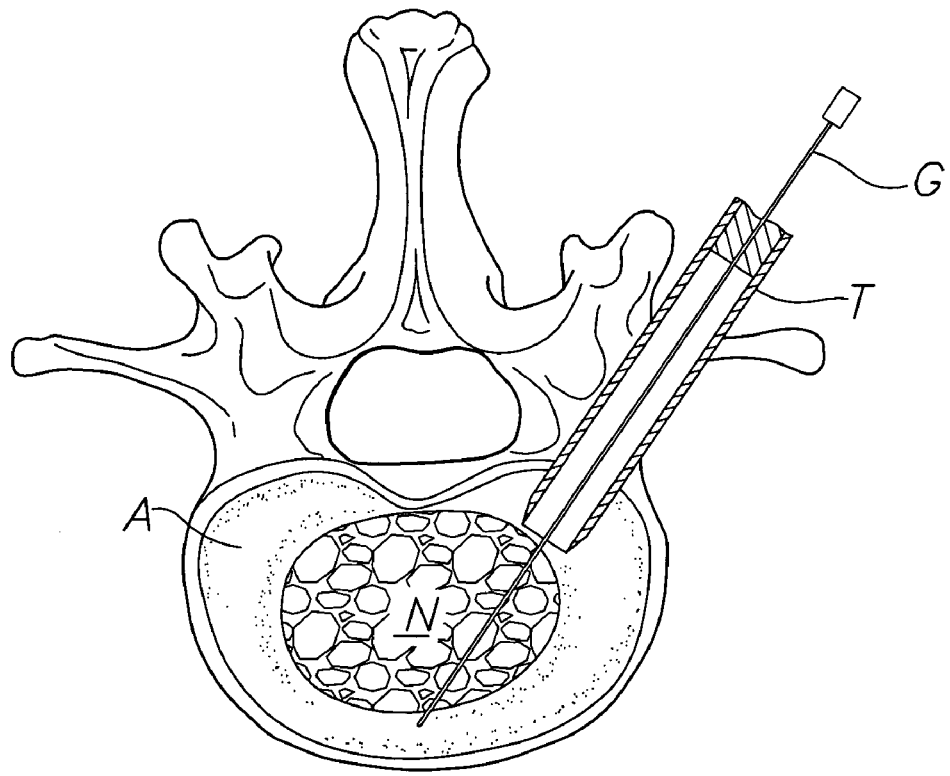
FIG. 3 is a sagittal view of the disc space shown in FIG. 2 with a trephine forming a portal in the annulus fibrosus of the disc.
Figure 4:
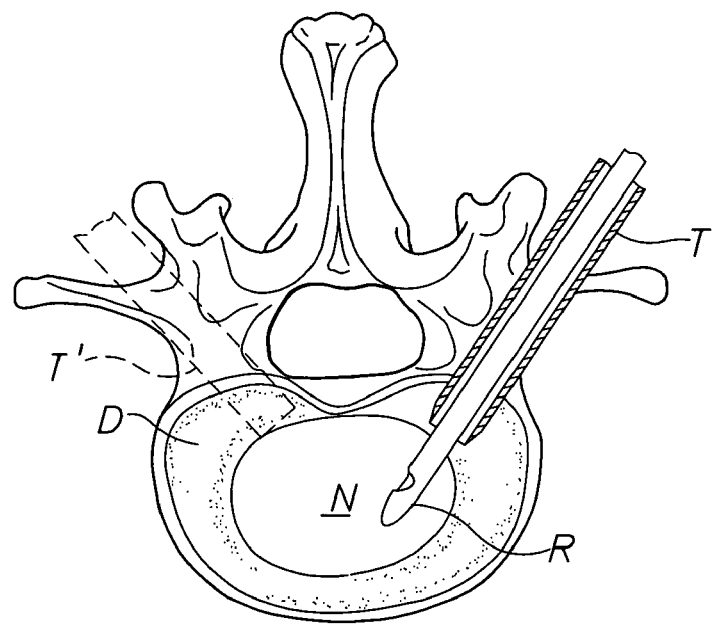
FIG. 4 is a sagittal view of the disc space shown in FIG. 3 with a tissue extraction device positioned within the nucleus pulposus of the disc.

A typical percutaneous discectomy procedure is illustrated in FIGS. 2-4. In the first step, a guide wire G is directed into an affected disc D between two vertebrae, such as the L2 and L3 lumbar vertebrae. As shown in FIG. 3, the guide wire G penetrates the annulus fibrosus A and the nucleus pulposus N, and it preferably anchored at opposite sides of the annulus A. The guide wire G can be positioned and placed under indirect vision, such as fluoroscopy, or stereotactically, or using other known procedures for properly orienting the guide wire within the spinal disc D. The procedure shown in the figures utilizes a posterior approach, which is preferable for implementation of the present invention. Of course, other approaches may be utilized for the discectomy in accordance with known surgical procedures. In addition, the access location may be dictated by the location of a fissure or herniation of the disc.

A trephine T is advanced over the guide wire and driven through the annulus A, thereby forming a portal into the disc nucleus. As shown in FIG. 4, a tissue removal device R can be advanced through the trephine T or through a working channel cannula aligned with the disc portal. The device R can then be used to remove all or part of the nucleus N of the disc D. As depicted in dashed lines in FIG. 4, a second trephine T' can be used to create a second annular portal to facilitate complete removal of the nucleus pulposus of the disc. The tissue removal device R can be of a variety of types, such as a rongeur, tissue morcellator, rotary and/or reciprocating vacuum-assisted cutter, and even a chemical introducer to direct a chemical such as Chymopapain into the nuclear space. Removal of the nucleus leaves a cavity C (see FIG. 5) surrounded by the substantially intact annulus A The present invention contemplates the introduction of a biomaterial into the disc cavity C that is capable or restoring disc height and preferably substantially normal disc function. For instance, any of the biomaterials discussed above can fill the newly formed cavity. In accordance with the preferred embodiment, the biomaterial is a fluid with an appropriate flowability and/or viscosity. In particular, the biomaterial must have sufficient flowability to permit relatively easy introduction into the disc cavity C, but with sufficient viscosity to hold its shape within the disc. Since the material being used to fill the disc cavity C is a fluid, the present invention provides means for holding a proper disc height as the material flows into the cavity, to thereby ensure that the cavity is filled—i.e., that the volume of implant biomaterial is the same as the volume of nucleus pulposus removed in the discectomy. Moreover, the methods and devices of the invention provide a means for maintaining the cavity volume as the biomaterial transforms to its solid state.

Thus, in accordance with one embodiment of the invention, a cannulated distractor 10 is provided as shown in FIGS. 5-8. The distractor 10 includes a distal end 12 that extends into the disc cavity C and a proximal end 14 that is configured to engage a device for injecting the biomaterial into the disc space. The distractor 10 includes a cannula 11 that terminates in a distraction tip 18 at the distal end of the device. A lumen 16 is defined along the entire length of the device from the proximal end 14 to the and through the distraction tip 18. The distraction tip 18 is sized to extend through the portal formed in the disc annulus A (see FIG. 3). The distractor 10 can include a shoulder 20 proximal to the distraction tip 18, in which the shoulder is sized to prevent passage through the annular portal. The shoulder 20 can operate to limit the distance that the distraction tip 18 extends into the disc cavity C. The distractor 10 can be provided with means for temporarily fixing the distractor in position or supporting the distractor on the adjacent vertebrae.

As shown in FIG. 7, the distraction tip 18 is intended to be inserted through the annular portal and is configured to restore the appropriate intradiscal height in the cavity C. Thus, in one embodiment, the distraction tip 18 can include a tapered leading portion 24. This leading portion 24 can be introduced into the cavity C and as the tip is advanced further into the cavity the leading portion will gradually distract the adjacent vertebrae as the leading portion 24 bears against the disc endplates E. In a specific embodiment, the tapered portion 24 can be substantially bullet-shaped, as shown in FIG. 8. With this configuration, the distraction tip 18 can have any rotational orientation when the tip is inserted through the annular portal.

Alternatively, the distraction tip can be configured like the tip 40 shown in FIG. 9. With this embodiment, the tip includes opposing generally flat sides 50 and intermediate edges 52 of the wedge portion 42. The tip 40 can be introduced into the disc space with the flat sides 50 of the wedge facing the disc endplates E. Once the tip is fully within the disc cavity C, the tip can be rotated so that the edges 52 contact and distract the endplates. The edges 52 themselves can be wedge-shaped, having a greater width at their proximal end than at their distal end.

Returning to FIGS. 6-8, in accordance with one feature of the invention, the distraction tip 18 includes a number of side orifices 30 and an end orifice 32 that all communicate with the central lumen 16. As depicted in FIG. 7, the orifices 30, 32 provide an exit path for fluid injected through the lumen 16. Preferably, the orifices are oriented to be unobstructed by the vertebral endplates E. The distraction tip 40 shown in FIG. 9 is also provided with side orifices 46 in the flat sides 50 and an end orifice 48. With this embodiment, the edges 52 need not include orifice(s) because the edges will be occluded by contact the endplates.

Since fluid is intended for introduction through the distraction tip 30, it is preferable that some feature be provided to ensure a substantially fluid-tight seal at the entrance to the disc cavity C through the annular portal. Thus, in one embodiment of the invention, the distraction tip 30 can include annular rings 26 that are intended to bear against the disc endplates E and/or the disc annulus A in a sealing relationship. The rings 26 can be integral with the distraction tip 30, or can be separate components mounted on the distraction tip, such as in the form of elastomeric seal rings. The seal rings can be mounted within annular grooves formed in the distraction tip.

Figure 10:
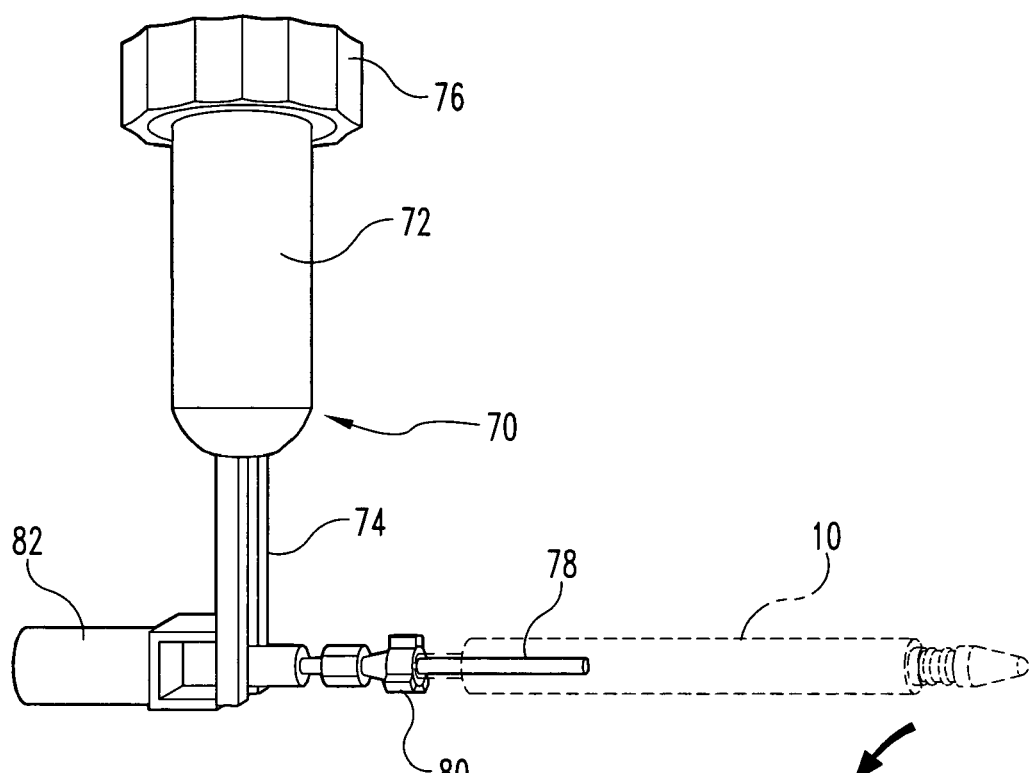
FIG. 10 is a side view of an injector apparatus for use in one embodiment of the invention.

The distractor 10 includes a fitting 36 defined at the proximal end 14 of the cannula 11. The fitting 36 provides means for making a fluid-tight connection with a device adapted to inject the biomaterial into the disc. One exemplary device 70 is shown in FIG. 10. The injector 70 includes a chamber 72 for storage of the biomaterial. In some cases, the chamber 72 may constitute multiple chambers where the injectable biomaterial is obtained by mixing various constituent materials. For instance, certain materials may be curable in situ and may require combining a curing agent with a base material. To facilitate mixing of the biomaterial constituents, the injector 70 can include a mixing chamber 74. A manual control 76 can be provided that forces the contents of the chamber 72 into the mixing chamber 74. Alternatively, the injector 70 can incorporate a mechanism that drives the fluid from the injector under pressure, such as a syringe or a pump.

The injector 70 includes a fitting 80 that is configured for fluid-tight engagement with the fitting 36 of the cannulated distractor 10. In a preferred embodiment, the two fittings 36, 80 represent mating components of a LUER® fitting. The injector can include a nozzle 78 that extends into the cannula 11, or more specifically into the lumen 16, when the injector 70 is engaged to the cannulated distractor. A grip 82 can be provided to allow manual stabilization of the injector.

Figure 5:
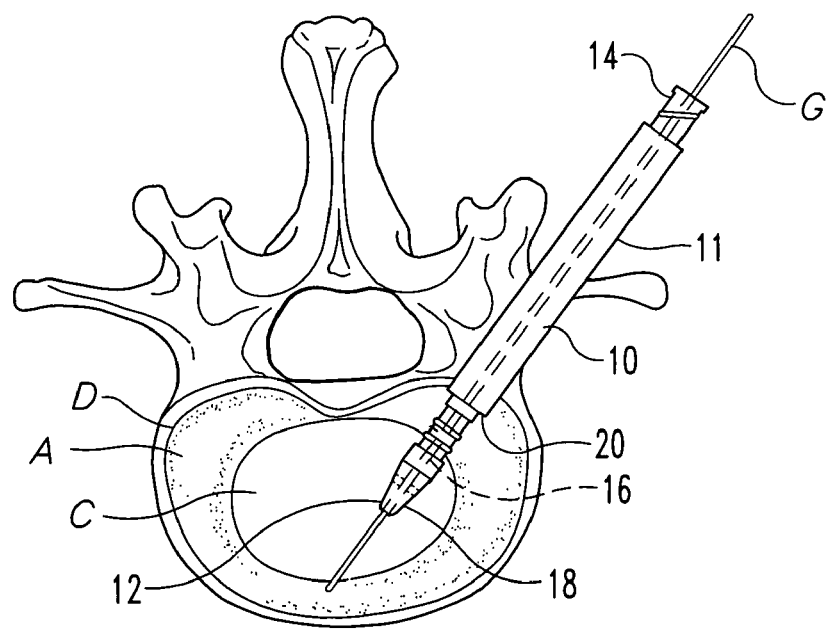
FIG. 5 is a sagittal view of the disc space shown in FIGS. 2-4 with a cannulated distractor in accordance with one embodiment of the present invention.

As explained above, the cannulated distractor 10 of the present invention may be utilized after a discectomy procedure. For purposes of illustration, it has been assumed that a total discectomy has been performed in which substantially all of the nucleus pulposus has been removed, leaving a disc cavity C as shown in FIG. 5. Of course, the principles of the invention can apply equally well where only a portion of the disc nucleus has been removed through a partial discectomy. If a bilateral approach has been used (as represented by the first and second trephines T and T'), one of the annular portals can be sealed with a material compatible to the disc annulus fibrosus. When the nucleus has been cleared, the guide wire G can be repositioned within the disc D, again preferably using known guidance and positioning instruments and techniques. The cannulated distractor 10 can then be advanced over the guide wire until the distraction tip 18 is properly situated within the nuclear cavity C. Preferably, the proper depth for the distraction tip 18 can be determined by contact of the shoulder 20 with the outer annulus A, or by contact of an associated depth feature with the adjacent vertebral bodies.

With the distraction tip 18, the tapered portion 24 gradually separates the adjacent vertebral endplates E as the distraction tip is driven further into the disc space. A mallet, impactor or other suitable driver can be used to push the tapered portion 24 into position against the natural tension of the disc annulus. It is understood that the goal of this step is to fully distract the intervertebral space to a proper disc height for the particular spinal level. For instance, for the L2-L3 disc space, the appropriate disc height may be 13-15 mm, so that the distraction tip is positioned within the cavity C to achieve this amount of distraction. As shown in FIG. 5, preferably only one cannulated distractor 10 is utilized, since the distraction tip 18 necessarily occupies a certain portion of the volume of the cavity C. However, a second cannulated distractor and associated distraction tip may be necessary (such as through a second annular portal as shown in FIG. 4) to achieve the proper disc height.

It should be understood that the process thus far would be similar for the distraction tip 40. However, unlike the tapered distraction tip 18, the distraction tip 40 requires an additional step to distract the disc space. Specifically, the distraction tip 40 is initially inserted with its flat sides 50 facing the endplates E. The tip must then be rotated until the edges 52 bear against and support the endplates. The flat sides 50 can include an angled transition to the edges, or the edges 52 can be rounded to facilitate the distraction as the distraction tip is rotated in situ.

When the distraction tip, such as tip 10, is inserted to its proper depth within the disc cavity C, the annular portal is sealed, whether by contact with the shoulder 20, or by engagement of the rings 26 with the endplates E or the interior of the annular portal. At this point, the biomaterial fluid can be injected into the cannulated distractor, and specifically into the lumen 16. To accomplish this step, the injector, such as injector 70, can be mated with the fitting 36 at the proximal end 14 of the cannulated distractor. Optimally, the guide wire G is removed and the fitting 80 of the injector engages the fitting 36. The nozzle 78 extends into the lumen 16. The nozzle can be sized so that the exit end of the nozzle is near or within the distraction tip 18. At this point, the injector 70 can be actuated in accordance with its construction so that the biomaterial fluid is displaced from the injector and into the lumen 16. The biomaterial exits through the orifices 30, 32 in the distraction tip 18 to fill the cavity C. The orifices 30, 32 are preferably positioned and sized to achieve complete and rapid dispersion of the biomaterial throughout the cavity. Again, the goal of this step of the process is to completely fill the entire volume of the cavity, or to replace the entire volume of nucleus pulposus removed during the discectomy. Where the fluid biomaterial is an in situ curable or settable material, time may also be of the essence to ensure a homogeneous mass once the material is completely cured.

It should be apparent that the distraction tip 18, 40 maintains the proper disc height while the biomaterial is injected. The tip can be retained in position until the injected material cures or sets. Once the material has sufficiently cured, the distraction tip 18, 40 can be removed. Since the distraction tip occupies a certain volume, additional biomaterial can be injected through the tip as it is being withdrawn, if required, thereby filling the gap left by the tip.

In certain embodiments, the distraction tip 18 can be a modular and removable from the cannula 11, as shown in FIG. 8. Thus, the tip 18 and cannula 11 can be provided with a removable mating element 19, such as a press-fit (as shown in FIG. 9) or a threaded or LUER® type fitting (not shown) as would occur to a person of skill in this art. A removable distraction tip can serve several purposes. In one purpose, the injected biomaterial may require a lengthy curing time. While the material is curing, it is of course necessary to keep the distraction tip in position to maintain the proper disc height. However, it may not be necessary to retain the other components of the system in position, such as the injector 70 and cannula 11. A modular distraction tip allows the cannula 11 to be removed while the tip remains in position, acting as a disc spacer while the biomaterial cures.

In another purpose, a number of differently sized tips can be mounted to a commonly sized cannula. Each patient has a different spinal anatomy, which means the appropriate disc height at a given spinal level may vary between patients. Moreover, the disc height can vary with spinal level. Thus, a plurality of differently sized distraction tips 18 can be provided to ensure proper spacing across the spinal disc D.

Another purpose behind a removable distraction tip 18 is achieved by embodiments in which the tip is formed of a biocompatible material that allows the tip to remain resident within the disc space. In this embodiment, the distraction tip material must be compatible with the biomaterial used to replace the natural nucleus. For instance, if the biomaterial is only intended to restore disc height, but not the natural biomechanical properties of the natural nucleus, then the material of the distraction tip 18 may provide a generally rigid scaffolding. On the other hand, and most preferably, the injected biomaterial is intended to emulate the biomechanical characteristics of the disc to allow the spinal segment to operate as close to a normal spinal segment as possible. In this instance, a rigid scaffold would of course frustrate the normal flexion, compression and torsional responses of the disc. Thus, the distraction tip 18 in embodiments where the tip is left in situ can be formed of a biodegradable or bioresorbable material that absorbs into the matrix of the cured biomaterial forming the disc nucleus prosthesis.

Whether the distraction tip is removed or remains within the disc space, it is preferable that the tip occupy as little volume as possible. On the other hand, the distraction tip must be sufficiently strong to sustain the compression loads that it will face while distracting adjacent vertebrae and holding the disc space height while the injected biomaterial cures. In the specific embodiments shown in FIGS. 5 and 7, the distraction tip 18 is shown traversing across a substantial portion of the nuclear cavity C. Alternatively, the distraction tip can have a reduced length from the shoulder 20 so that the tip extends only partially into the cavity. Distraction of the disc space can be abetted by certain positions of the patient on the operating table where, for instance, the anterior aspect of the disc space is naturally distracted by the position of the spine. Proper distraction of the disc space may be better accommodated by an anterior approach, rather than the posterior approach shown in FIGS. 5 and 7.

In alternative embodiments, the distraction tip can assume a wide range of geometries, some dictated by the annular portal formed during the discectomy procedure. In the embodiment of FIGS. 5-8, a circular annular portal has bee created and a circular distraction tip 18 utilized to seal the portal. In some cases, a planar or wedge-shaped distraction tip, similar to the tip 40 shown in FIG. 9, can be utilized where the opening through the annulus has an area greater than the tip itself. In these cases, the extra space between the tip and the interior surface of the portal can provide an opening for a direct visualization instrument, or some other appropriate instrument. Preferably, this approach is better suited where the biomaterial is not injected under pressure, such as cases where a gravity feed is employed (see FIG. 11 and associated discussion below).

Figure 12:
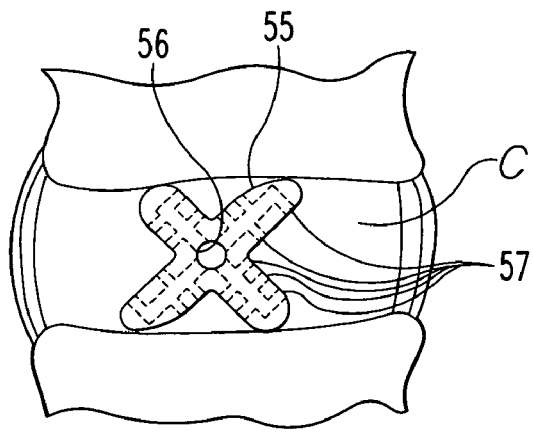
FIG. 12 is a cross-sectional view of a cruciate distraction tip according to one embodiment of the cannulated distractor of the present invention.

In other cases, surgeons perform the discectomy through rectangular or cruciate portals in the disc annulus. A complementary shaped distraction tip can be utilized to conform to and fill the annular portal. For instance, the distraction tip can assume the configuration shown in FIGS. 12-14. A cruciate-shaped tip 55 is shown in FIG. 12 with a central lumen 56 communicating with a number of openings 56. It is understood that the arms of the cruciate-shaped tip can have a thinner cross-section than shown in the figure, provided they are sufficiently strong to support the adjacent vertebrae in their proper distracted position. Likewise, the openings 56 can be distributed in a variety of patterns through the hub and legs of the cruciate shape.

Figure 13:
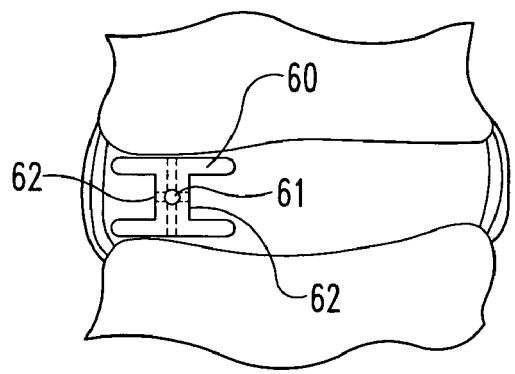
FIG. 13 is a cross-sectional view of an I-beam shaped distraction tip according to another embodiment of the cannulated distractor of the present invention.
Figure 14:
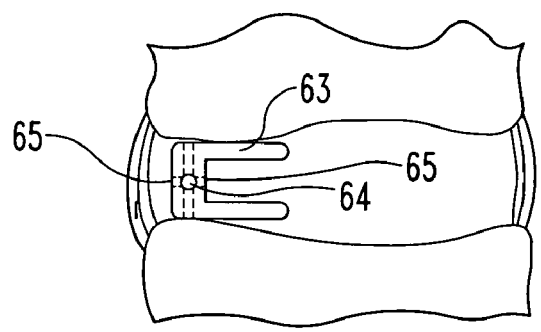
FIG. 14 is a cross-sectional view of a C-shaped distraction tip according to a further embodiment of the cannulated distractor of the present invention.

An I-beam distraction tip 60 is shown in FIG. 13 having a central lumen 61 communicating with a number of openings 62. The distraction tip 63 in FIG. 14 has a C shape and includes a lumen 64 and openings 65. These two beam configurations provide sufficient support for the necessary distraction. Again, the thickness of the arms of the beams can be reduced as necessary to minimize the cross-section of the distraction tip 60, 63.

Regardless of the overall configuration of the distraction tip, it is most preferable that volume of the tip within the nuclear cavity C be minimized. The bullet-shaped tip, such as tip 18, may be less desirable from that standpoint, while the wedge type, such as tip 40, may be preferable. In addition, regardless of the overall configuration, the distraction tip must communicate with the lumen 16 and must provide some means for discharge of the biomaterial fluid through the tip. In the illustrated embodiments, the distraction tips 18, 40 include orifices 30, 31 and 46, 48, respectively, that communicate with the corresponding lumens 16, 44. Alternatively, the distraction tips can be in the form of an open scaffold or skeletal framework. Again, the scaffold or framework must be sufficiently strong, especially in compression, to properly distract the disc space and hold the disc height for an appropriate length of time. In some embodiments, the distraction tip can be formed of a material having interconnected interstices, such as a porous material. The porous distraction tip can present a solid scaffold with a multitude of fluid flow paths through the material. The porous material can be a metal, such as a porous tantalum; however, a porous polymer, such as polylactic acid, is preferred so that the scaffold does not obscure visualization of the disc space after the procedure is completed.

In the procedures discussed above, the distraction tip has been described as providing an avenue for the injection of a biomaterial into the nuclear cavity C following a discectomy procedure. The distraction tips of the present invention serve equally well as a conduit for the introduction of other fluids to the disc space. For instance, the distraction tips can be used to inject a biomaterial such as the material disclosed in provisional application Ser. No. 60/336,332, entitled "Pretreatment of Cartilaginous Endplates Prior to Treatment of the Intervertebral Disc with an Injectable Biomaterial", mentioned above, the disclosure of which is incorporated herein by reference. This provisional application discloses materials for the pretreatment of the disc endplates, for instance, to improve the biological functioning of a degenerative disc. The cannulated distractors of the present invention, such as distractor 10, can be initially used for the disc pretreatments disclosed in the above-mentioned provisional application. Once the pretreatment has been completed, the cannulated distractor can then be used for the injection of the curable biomaterial.

Likewise, the present inventive cannulated distractor can be used for multiple fluid injections, including multiple injections to effect curing of a biomaterial within the nuclear cavity C. For instance, certain biomaterials may include a first constituent that is introduced into the disc space, followed by a second constituent or curing agent. The second constituent can initiate curing of the resulting composition.

Figure 11:
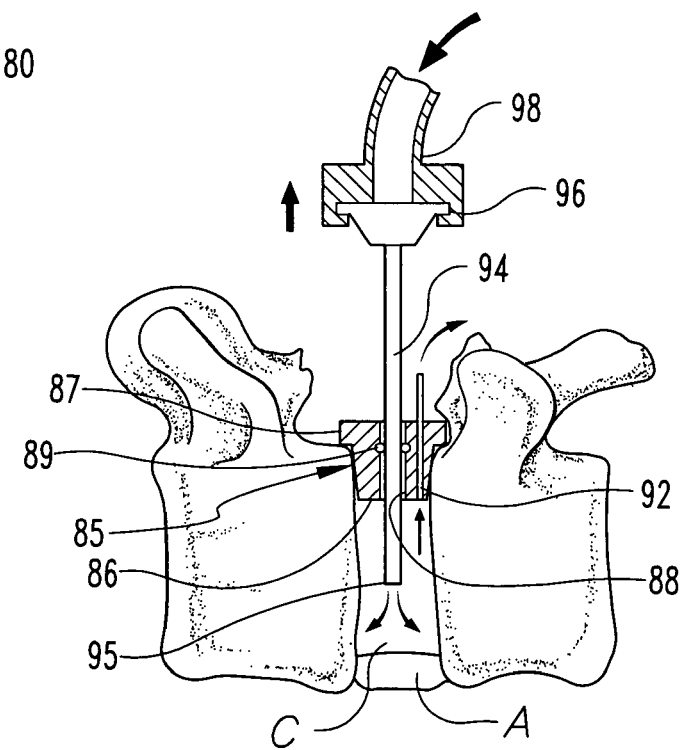
FIG. 11 is lateral view of a disc space with a cannulated distractor in accordance with a further embodiment of the invention.

An alternative embodiment of the invention is depicted in FIG. 11. In this embodiment, a cannulated distractor 85 is provided that includes a generally frusto-conical distraction tip 86 and a shoulder 87. The tip 86 is configured to act as a wedge to distract the disc space as the cannulated distractor 86 is impacted into the disc space. The shoulder 87 acts as a stop against the adjacent vertebral bodies to limit the distance that the tip is driven into the disc space. Preferably, the distraction tip 86 has a length from the shoulder 87 to its distal end that is sufficient to span the length of the portal in the disc annulus A, but is limited in its extent into the nuclear cavity C. With this embodiment, the distraction tip 86 does not displace any significant volume within the cavity C.

The cannulated distractor 85 defines a lumen 88 extending the entire length of the distractor. The lumen 88 is sized to receive an injection tube 94 therethrough. The injection tube 94 can include a fitting 96 for engaging an injection apparatus 98. The fitting 96 can be of any suitable type, such as the LUER® fitting mentioned above. The injection apparatus can be similar to the injector 70 shown in FIG. 10, or can assume a variety of configurations for the introduction of a fluid into the disc cavity. In one embodiment of the invention, the biomaterial fluid is introduced into the cavity by way of gravity feed. In this instance, the injection apparatus 98 can be simply in the form of a reservoir with an atmospheric vent to allow the biomaterial to flow downward into the disc space by gravity alone. Of course, the patient must be properly presented to accommodate gravity filling of the disc cavity C.

In this embodiment, the cannulated distractor 85 operates as a support or guide for the injection tube 94. The tube 94 can be in the form of a smooth tipped, relatively large gauge needle that is sized to accommodate optimum flow of the biomaterial into the disc space. The tube 94 can be introduced through and gradually withdrawn from the cannulated distractor 85 (as indicated by the arrow in FIG. 11) as the biomaterial flows into the cavity C. In addition, the diameter of the tube 94 can be sized relative to the diameter of the lumen 88 so that the discharge opening 95 of the tube 94 can be pivoted with a sweeping motion through the cavity C. This aspect of this embodiment facilitates complete direct filling of the disc cavity C with the biomaterial. Where the cannulated distractor is used to introduce pre-treatment materials, such as those discussed above, this feature allows positioning of the discharge opening 95 to direct the pre-treatment materials where they are needed.

In certain embodiments, the lumen 88 can be provided with a seal 89, which can be in the form of an elastomeric seal ring. The seal 89 can form a fluid-tight seal around the injection tube 94, which can be especially important where the biomaterial is injected under pressure. In addition, the seal 89 can operate as a form of joint to support the injection tube 94 as the discharge opening 95 is manipulated within the disc cavity.

In another feature of the invention, the cannulated distractor can provide a vent for the discharge of excess biomaterial when the disc cavity C is full. The vent is particularly useful where the biomaterial is introduced under gravity feed. In one specific embodiment, a vent hole 92 is provided in the distractor 85. When the disc cavity is full, the biomaterial will seep through the vent opening 92, providing a direct visual indication that the cavity is full. Preferably, the vent opening 92 includes a tube that projects away from the cannulated distractor 85 to improve the visibility of the vent in situ. Alternatively, the vent can be formed by a difference in diameter between the injection tube 94 and the lumen 88, and in the absence of the seal 89.

The vent 92 is well-suited to procedures involving gravity feed of the biomaterial into the disc space. However, the vent can also be useful where the material is fed under pressure. For example, the vent 92 can be maintained initially open as the biomaterial is injected into the cavity C through the injection tube 94. When the cavity is completely full, biomaterial will seep from the vent 92. As this point, the vent can be closed and additional biomaterial injected into the disc space to increase the pressure within the cavity C. The seeping through the vent provides an immediate indication that the cavity is full, and can provide a starting point for the introduction of a calibrated amount of additional biomaterial to achieve a proper cavity pressure.

With each of the embodiments, once the biomaterial has cured and the cannulated distractor removed, the portal or portals in the disc annulus can be filled to prevent herniation of the newly formed prosthetic disc material. The annular portal can be sealed with any suitable material, such as fibrin glue, or a polymerizable material, or the like. The material used to seal the annulus should be sufficiently strong to remain intact as the intradiscal pressure is increased due to hydration or biomechanical movement of the spine.

In accordance with certain embodiments, the cannulated distractors, and particularly the distraction tips, described above can be formed a variety of bio-compatible materials. As explained above the distraction tips must be sufficient strong to maintain proper distraction of the disc space until the biomaterial has been fully injected and cured, if necessary. In certain embodiments, the distraction tips are formed of a bio-compatible metal, such as stainless steel or titanium. In other embodiments, the distraction tips are formed of a polymer or plastic that is preferably radiolucent to permit visualization of the distraction tip in situ to verify the position of the component.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method of introducing a fluent material into a disc space to replace disc nucleus pulposus within the disc annulus fibrosis, comprising the steps of:

creating an opening having a first extent through the annulus fibrosis of a spinal disc in communication with the intradiscal space;

removing at least a portion of nucleus pulposus;

providing an integral tube unit comprising an elongate tube having a distal end and an opposite proximal end and a seal supported integrally on said tube adjacent the distal end, said seal including a surface having a second extent greater than said first extent projecting outwardly from said tube;

moving said tube unit toward said annulus fibrosis until said distal end of said tube extends through said opening and into said intradiscal space and said seal surface engages said annulus fibrosis adjacent said opening in a sealed relationship;

introducing fluent curable biomaterial in a liquid form through said tube directly into said intradiscal space in contiguity with said annulus fibrosis or remaining nucleus pulposus, said material having properties that upon curing are substitutive of the nucleus pulposus; and allowing said fluent biomaterial to substantially cure while maintaining said seal.

2. The method of claim 1, wherein the step of introducing fluent said biomaterial comprises introducing the material under pressure.

3. The method of claim 2, wherein said pressure is substantially maintained until the biomaterial is cured.

4. The method of claim 1, comprising the step of further providing said tube unit with a vent through said seal separate from said tube for communication with said intradiscal space.

5. The method of claim 4, wherein the biomaterial is introduced into the intradiscal space until the biomaterial seeps from said vent, and further comprising the step of closing said vent upon seepage of biomaterial from the vent to thereby increase the pressure of biomaterial in the disc space.

6. The method of claim 1, further including the step of distracting the vertebral bodies apart to increase disc height.

7. The method of claim 6, wherein the distraction step is performed by a separate distractor.

8. The method of claim 7, wherein said distractor is defined by the distal end of said tube, said distal end being sized and configured to provide distraction of opposed vertebrae communicating with said disc space.

9. The method of claim 1, wherein said seal comprises at least one elastomeric ring.

10. The method of claim 9, wherein said seal comprises a plurality of elastomeric rings spaced longitudinally along the distal end of said tube.

11. The method of claim 1, further including the step of removing said tube from said opening and said seal surface from said annulus fibrosis after said material is substantially cured.

12. A kit of parts for sealably introducing fluent material directly into the disc space through an opening having a first extent extending through the annulus fibrosis of said disc, comprising:

an integral tube unit including an elongate tube having a passageway for the flow of fluent material therethrough and a distal extent adapted to be received in the opening of said annulus fibrosis, said tube supporting a seal integrally thereon, said seal including a surface having a second extent greater than said first extent projecting outwardly from said tube and being sized and configured to engage said annulus fibrosis adjacent said opening to form a fluid-tight seal therewith, and a vent extending through said seal separate from and adjacent said tube and arranged to communicate with said disc space; and a quantity of curable fluent material adapted to be introduced in a fluid state into said disc space through the passageway of said tube, said material upon curing having properties substitutive of the nucleus pulposus.

13. The kit of parts according to claim 12, wherein said fluent material is a curable biomaterial selected from the group of nucleus pulposus substitutes consisting of hyaluronic acid, fibrin glue, alginates, elastin copolymers and collagen gels.

14. The kit of parts according to claim 12, wherein said distal extent comprises at least one orifice communicating with said passageway to provide an exit path for said fluent material into said disc space.

15. The kit of parts according to claim 14, wherein said distal extent includes a distal tip removable from said tube.

16. The kit of parts according to claim 15, wherein there are a plurality of removable distal tips, each being of different size.

17. The kit of parts according to claim 15, wherein said distal tip is formed of bioresorbable material.

18. The kit of parts according to claim 12, further including a syringe adapted to inject said fluent material into the passageway of said tube.

19. The kit of parts of claim 12, wherein said seal further including a portion sized to reside within said opening of said annulus fibrosis.

20. The kit of parts of claim 12, wherein said seal comprises at least one elastomeric ring.

21. The kit of parts of claim 20, wherein said seal comprises a plurality of elastomeric rings spaced longitudinally along the distal end of said tube.

* * * * *